United States Patent
Kristensen

[11] Patent Number: 5,935,116
[45] Date of Patent: Aug. 10, 1999

[54] GARMENT FOR FIXING A URINE BAG AND A METHOD FOR MANUFACTURING SUCH GARMENT

[75] Inventor: Johannes Nyvang Kristensen, Ikast, Denmark

[73] Assignee: Tytex A/S, Ikast, Denmark

[21] Appl. No.: 08/913,054
[22] PCT Filed: Apr. 23, 1996
[86] PCT No.: PCT/DK96/00182
  § 371 Date: Sep. 5, 1997
  § 102(e) Date: Sep. 5, 1997
[87] PCT Pub. No.: WO96/33675
  PCT Pub. Date: Oct. 31, 1996

[30] Foreign Application Priority Data
  Apr. 24, 1995 [DK] Denmark .................. 0479/95

[51] Int. Cl.[6] .............. A61F 5/44; A41B 11/00; A41B 9/08
[52] U.S. Cl. .............. 604/353; 604/345; 2/242; 2/22; 66/175; 66/176
[58] Field of Search ............ 66/175–178; 2/22, 2/169, 239, 242, 402, 403, 404, 406, 407; 604/345, 353, 349

[56] References Cited
U.S. PATENT DOCUMENTS
4,352,356 10/1982 Tong .
5,375,265 12/1994 Selzer .

FOREIGN PATENT DOCUMENTS
4113133 2/1993 Germany .

OTHER PUBLICATIONS
International Publication No. WO 86/05969 to K. Thomsen entitled, "Urine Bag Holder," Oct. 23, 1986.

*Primary Examiner*—Robert A. Clarke
*Attorney, Agent, or Firm*—Watson Cole Grindle Watson, PLLC

[57] ABSTRACT

A garment (1) is disclosed for fixing a urine bag (2) on the leg (3) of a user. The garment includes a tubular part (6) having elastic bands (9, 10) at its ends, said bands fitting tightly around the leg (3) of the user. The tubular part is provided with an integrally formed pocket (11), the tubular part being formed by a dual layer knitted structure except in the area of the pocket (11). At the pocket bottom (13) there is an opening (14) for the discharge pipe (15) of the urine bag. The garment (1) is manufactured easily in endless webs, which are separated, and subsequently the two end edges (31, 32) are knitted together (33) in order to form the tubular shape. The garment provides safe fixing of the urine bag (2) as the latter will be supported inside the pocket (11) and be held against the leg of the user due to the elastic bands (9, 10), which are dimensioned so as to be able to carry a full urine bag. Owing to the use of elastic threads across the height of the garment, the full urine bag is held against the leg of the user without collapsing.

10 Claims, 3 Drawing Sheets

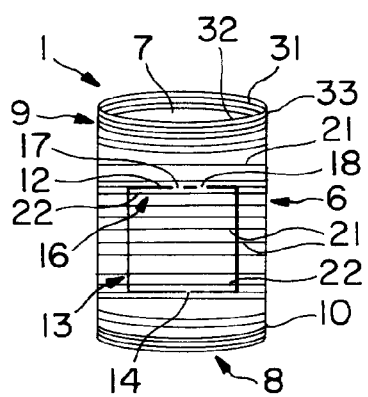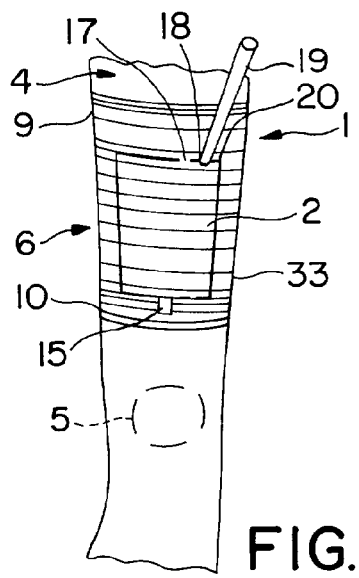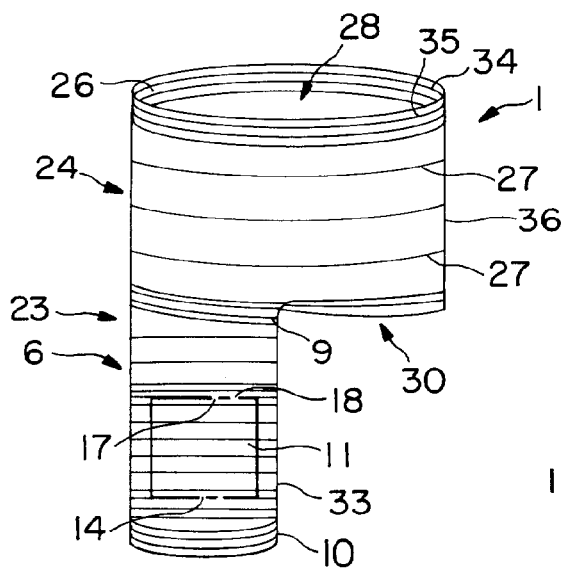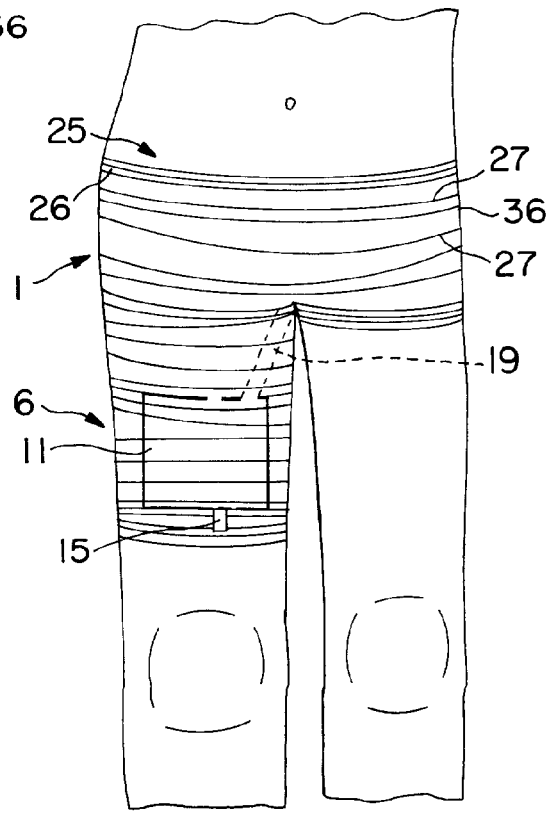

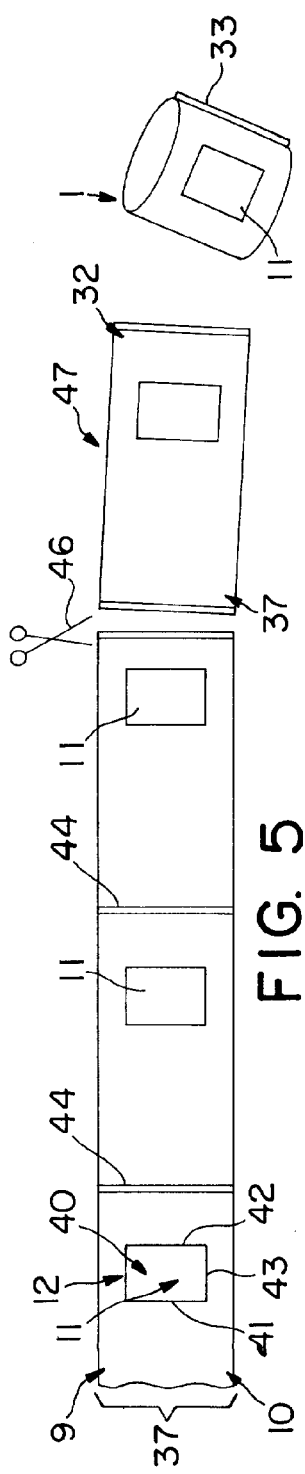
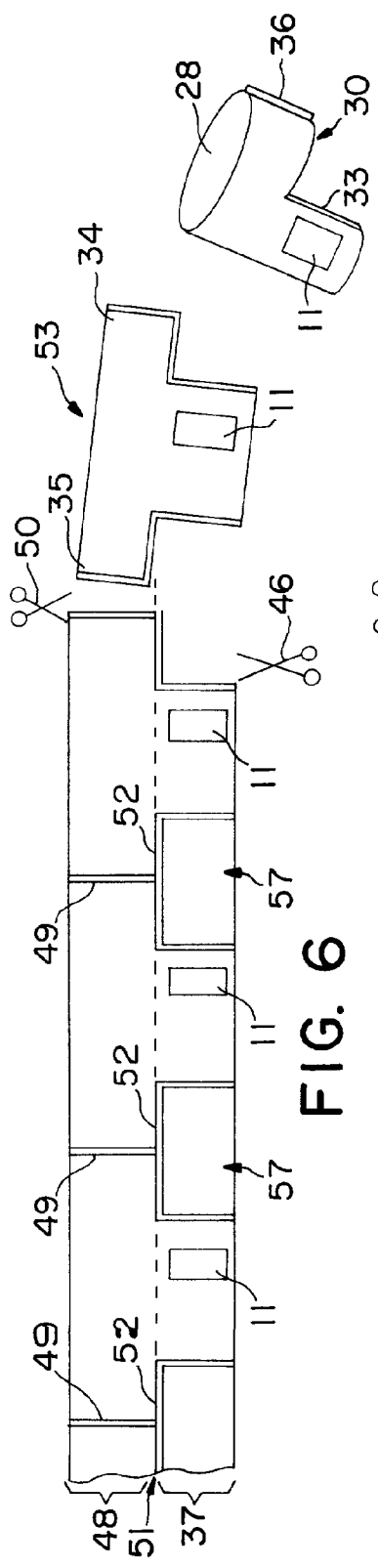
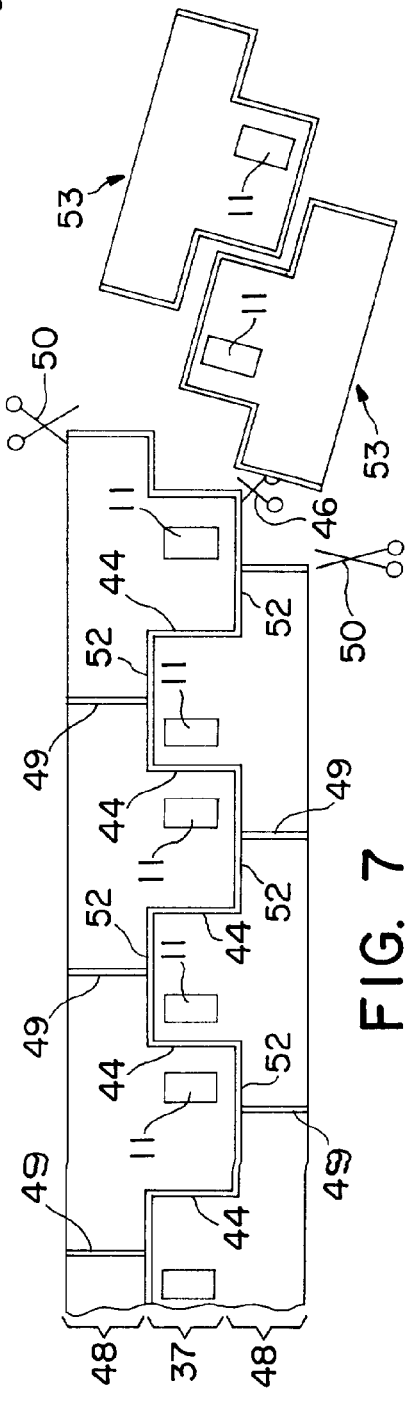

GARMENT FOR FIXING A URINE BAG AND A METHOD FOR MANUFACTURING SUCH GARMENT

BACKGROUND OF THE INVENTION

1. Field of Invention

The present invention relates to a garment for fixing a urine bag on the leg of a user, preferably on the front of the user's thigh, and including at least one tubular part to be positioned on the leg of the user, and which is manufacturing by knitting.

The invention further relates to a method for manufacturing a garment for fixing a urine bag on the leg of a user, preferably on the front of the user's thigh.

2. The Prior Art

Such a garment for placing on the thigh of a user is known, e.g., from German patent publication No. 4,113,133. This patent publication discloses a knitted garment consisting of a tube. In order to fix a urine bag, it must be placed on the outside of a tube section, and subsequently the remaining part of the tube is folded over the urine bag and the first section of the tube. Thus, positioning the urine bag is difficult.

Putting it on would also involve some difficulty when the tube is pulled in a stretched state over the foot and the leg. Thus, the free end of the tube may become tight against the leg and impede pulling up. If, instead, the tube is rolled up into an annular shape for pulling over the leg, it will subsequently be difficult to straighten out the tube so that it has sufficient length over the thigh and knee of the user.

The known garment is further disadvantageous in that it only provides partial fixing of the urine bag. Thus, the urine bag will be positioned in the space between the two overlying tube sections. This space forms an annular chamber. The urine bag will be able to move within this pocket. The only fixing of the urine bag obtained in relation to the garment is established by the passage of a discharge pipe through an opening in the intersection of the two tube sections. It is undesirable that the bag is thereby able to "tilt" as there is a risk that the inlet pipe will disengage from a catheter. At the same time it will involve a considerable disadvantage to the user that the fastening of the upper end of the urine bag is accomplished by the catheter. This may be particularly uncomfortable with a full urine bag.

It is the object of the present invention to provide a garment that remedies the abovementioned disadvantages and which is easy and simple to use while at the same time obtaining a secure and reliable fixing of the urine bag to the leg of a user. It is a further object of the invention to provide a method for the manufacture of such a garment, which may be manufactured in endless webs with a minimum of subsequent tailoring.

SUMMARY OF THE INVENTION

This is obtained according to the present invention by a garment characterised in that the tubular part includes elastic bands at its ends and arranged to be able to carry a full urine bag, and that a pocket is produced as an integral part of the tubular part, which has a dual layer structure that is knitted together except in a central area for the pocket, that the pocket has an upward oriented opening in the service position, and that at the bottom oriented downward in the service position the pocket has at least one opening for the passage of a discharge pipe of the urine bag.

As the tubular part comprises elastic bands, the garment and, consequently, the pocket containing the urine bag will be held tight against the leg of the user even if the urine bag is full. Fixing may be against the user's thigh as well as his tibia. The tubular part is simply manufactured with dimensions corresponding to the thigh or tibia and with a pocket, which may have the same size in different sizes of the tubular part.

As the tubular part comprises a pocket, secure fixing of the urine bag is obtained. With a suitable dimensioning of the pocket for the size of the urine bag, the urine bag will be prevented from "tilting", and the urine bag will stand steadily due to the pocket surrounding the urine bag.

The urine bag may easily be positioned in the pocket through the upward oriented opening once the user has placed the tubular part around his leg. The tubular part only needs to have a length corresponding to the height of the urine bag. This reduces the risk that the tube would become tight against the leg when the tube is pulled over the foot and leg in order to be placed around the thigh or the leg below the knee. Even if the tubular part is not positioned quite smoothly, it will still be easy to place the urine bag in the pocket. The tubular part will stretch and be positioned smoothly on the leg as the urine bag is placed in the pocket. The discharge pipe of the urine bag passes through an opening in the bottom of the pocket so as to make it possible to empty the urine bag without removing the urine bag from the pocket.

A method making it possible to manufacture the garment in endless webs is characterised in that a first web is knitted on two needle tracks, that the first web is knitted of yarns from the two needle tracks except in a central area of a pocket having an upward oriented opening in the service position, that elastic bands are knitted at either edge area of the first web, that in a position between each subsequent pocket cutting lines are formed transversely of the knitted first web, that the first web is cut up in the cutting lines, and that the ends of the web sections thus formed are assembled for the formation of a tubular garment having such size that it will fit snugly around the leg of a user.

By this method the first web is knitted in endless webs on conventional flat knitting machines, preferably double Raschel machines. The only kind of subsequent tailoring needed is the mutual assembling of the ends of the web sections, preferably by sewing in order to form the tubular garment.

The web is preferably formed by means of two sets of latch needles and the various laying tracks. By different types of knitting these will form the pocket, the bands, the opening for the discharge pipe and the cutting lines.

Alternatively, it is also possible to assemble the ends of the web sections by other fastening means, such as bur locks, press buttons, snap fasteners or similar devices. This makes it possible to apply the garment to a user with whom pulling it over the foot and leg is impossible. For example this could be the case with seriously disabled persons or persons having their legs in plaster.

According to a preferred embodiment, elastic threads will be knitted in across the height of the pocket at a mutual distance and extending in the circumferential direction of the tubular part. Such elastic threads will help to keep a full urine bag tight against the leg of the user. This reduces the risk of splashes, and at the same time the urine bag is prevented from "caving in" at increased load. The elastic threads will also help to fix the urine bag. Thus, the elastic threads will reinforce the effect obtained by the elastic bands. In this manner it is possible to distribute the pressure to be exercised over a larger area. This ensures the user a more unhampered blood circulation, and at the same time the discomfort that may result from tight elastic bands is reduced.

The edge area at the upward oriented opening of the pocket is preferably provided with a number of holes for the passage of the inlet pipe of the urine bag. Owing to this arrangement, the pocket may be designed to contain different types of urine bags having their inlet pipes located centrally or in a lateral area. Such a hole in the edge area will further help to orient the inlet pipe correctly in the direction of a catheter. Thus, preferably there will be at least one hole located at the corner that in use faces the opposite leg of the user. This will cause the inlet pipe of the urine bag to be oriented directly towards a catheter. Such a garment will be comfortable to the user.

The invention will now be explained in detail with reference to the accompanying schematic drawings.

BRIEF DESCRIPTION OF THE DRAWINGS

FIG. 1 shows a view of a first embodiment of a garment according to the invention;

FIG. 2 shows a view of a second embodiment of the garment according to the invention;

FIG. 3 shows a view illustrating the garment shown in FIG. 1 when in use;

FIG. 4 shows a view illustrating the garment shown in FIG. 2 when in use;

FIG. 5 shows a schematic illustration of a first embodiment of a method according to the invention;

FIG. 6 shows a schematic illustration of a second embodiment of a method according to the invention;

FIG. 7 shows a schematic illustration of a third embodiment of a method according to the invention.

DETAILED DESCRIPTION OF THE PREFERRED EMBODIMENTS

Figure 8:
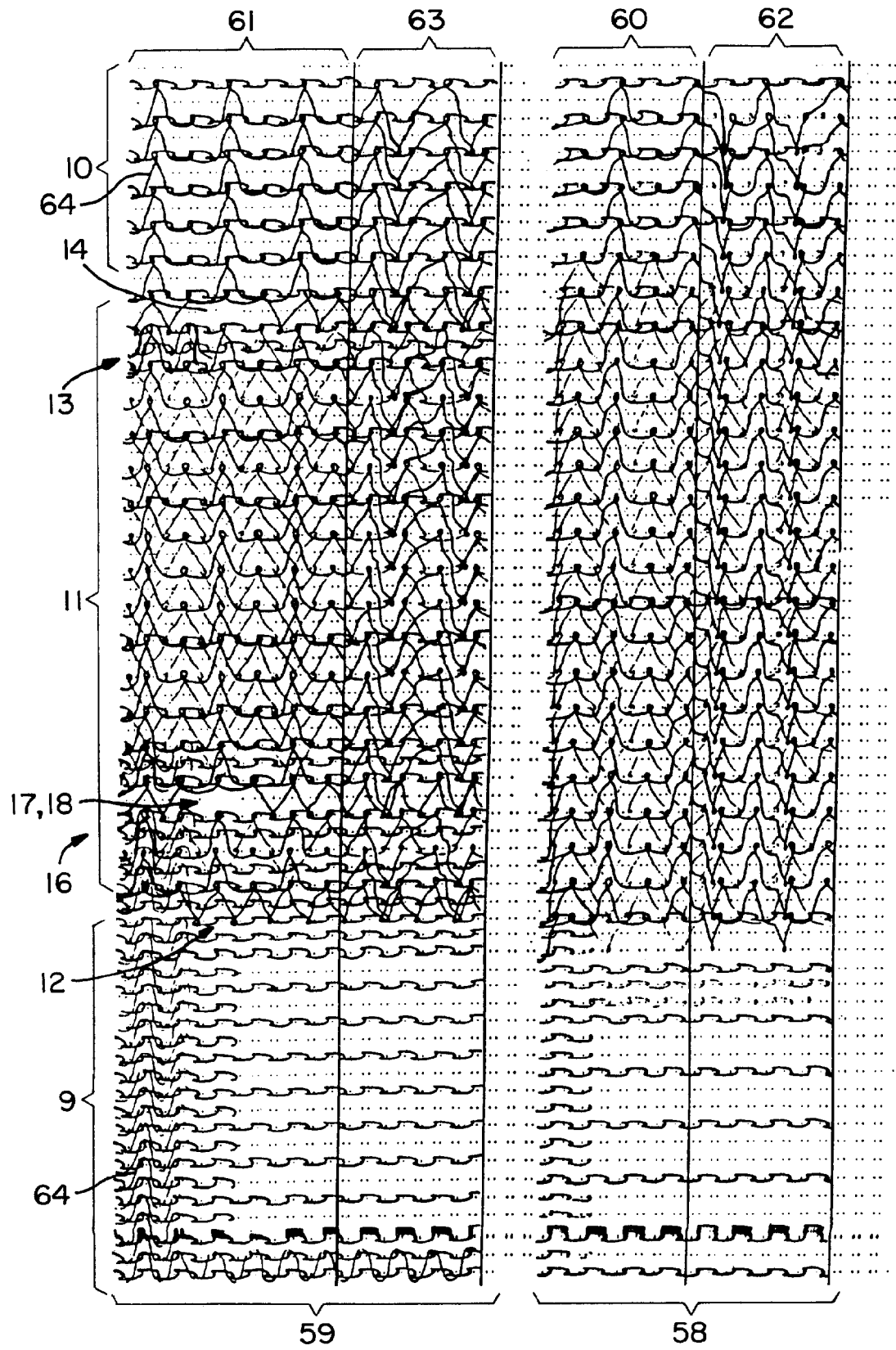
FIG. 8 shows a partial knitting diagram for illustration of the knitting in the formation of a pocket.

Identical reference numerals will be used in different figures to designate corresponding or identical items. A detailed explanation of these items will not be given for each embodiment.

FIGS. 1 and 3 illustrate a first embodiment of a garment 1 according to the invention The garment is designed to fix a urine bag 2 on the leg 3 of a user. In the embodiment shown it is fixed against the thigh 4 of the user. Alternatively, it is possible to fix the urine bag on the leg of the user below the knee 5. In the position shown the urine bag 2 is placed on the front of the right thigh 4.

The garment 1 comprises a tubular part 6 dimensioned so as to be placed against the thigh 4 of the user. The garment 1 is manufactured by knitting. The tubular part 6 is provided at either open end 7, 8 with an elastic knitting forming a band 9, 10 in the edge areas, which delimit the openings 7, 8. The elastic bands 9, 10 will keep the garment tight against the thigh 4 of the user.

The tubular part 6 is provided with a pocket 11, which is produced as an integral part of the remaining tubular part 6, the latter being produced with a dual layer structure. As it is knitted on a double Raschel knitting machine, the web of the tubular part 6 is knitted together across its total extension except at the pocket 11. The pocket 11 is dimensioned such that the urine bag 2 will fit inside the pocket and is supported in lateral directions. The pocket 11 will preferably be placed in a central position on the tubular part. It should also be understood, however, that the pocket 11 may be placed in an upper or lower area of the tubular part 6. In a position for use the opening 12 of the pocket 11 will be oriented in upward direction and, therefore, will allow easy introduction and removal of the urine bag 2 without removing the garment.

At the bottom 13 of the pocket at least one opening 14 is formed for the passage of a discharge pipe 15 of the urine bag 2. A number of holes 17, 18 for the passage of an inlet pipe 19 of the urine bag 2 are positioned at an edge area 16 along the upward oriented opening 12. The holes may be placed in a central position, as indicated by 17, or displaced toward a corner 20 of the pocket, which will face the opposite leg of the user (see hole 18 in FIG. 3) when in use. As the inlet pipe 19 passes through this hole 18 positioned at the corner 20, it will be oriented directly toward a catheter so that the user has a more comfortable feel in use.

The tubular part is provided with a number of elastic threads 21 that are knitted in to extend in the circumferential direction of the tubular part 6. The threads 21 will at least extend across the height of the pocket 11, but in the embodiment shown they also extend over and under the pocket. These elastic threads will help to retain the urine bag in the pocket and thus distribute, the thrust load over a larger area. This improves the user comfort.

Colored elastic yarns 22 are knitted in at the bottom and the top of the pocket. This arrangement makes it easy for the user to find the position of the opening 12 as well as the position of the opening 14 for the discharge pipe 15 at the bottom 13 of the pocket 11.

FIGS. 2 and 4 show a second embodiment of the garment 1 according to the invention. This garment comprises a tubular part 6 substantially corresponding to the garment illustrated in FIGS. 1 and 3. The embodiment of FIGS. 2 and 4 differs in that the tubular part 6 is interknitted at its upper end 23 with a second tubular part 24 having a larger diameter dimensioned to fit around the waist 25 of a user. By this arrangement the garment may be conceived of as panty briefs with a long leg consisting of the tubular part 6. At their upper end these briefs will have a circumferential elastic band 26 and across their height they will be provided with a number of elastic threads 27 to hold the briefs tight against the abdomen of the user. The band 26 defines a waist opening 28, and at the bottom elastic threads will be knitted in corresponding to those used in the band 9 of the tubular part 1 so that a leg band 29 is formed, which defines a leg opening 30.

A urine bag 2 will be placed in the pocket 11 in the same manner as explained above. in the outward oriented edge area 16 around the opening 12 of the pocket. Instead, these openings 17, 18 will be positioned in the edge area facing the user so that the inlet pipe 19 is directed from the pocket 11 to the inside of the briefs.

A common feature of the embodiments shown is that they are formed by one web section, which is folded onto itself so that two ends 31, 32 may be assembled with each other, preferably by a seam 33 in order to form the closed tubular part 6. Similarly, two ends 34, 35 of the second tubular part 24 are sewn together. These two ends 34, 35 are also assembled with each other by a seam 36.

FIG. 5 illustrates that the garment 1 is manufactured from an endless first web 37. The first web 37 is manufactured from yarns from two needle tracks being interknitted except in a central area 40 for the formation of the pocket 11.

The first web 37 is produced by two needle tracks on a double Raschel knitting machine. The web is produced by latch needles and different laying tracks interknitting the yarns from the two needle tracks except in the area for the pocket 11. The pocket 11 is formed by the interknitting so that there is an assembly of the web formed by the two needle tracks at the two sides 41, 42 and the bottom 43 of the pocket. The end of the pocket intended to be upward oriented in use is not knitted together and, thus, an opening 12 is formed.

Further openings 14, 17 and 18 for the inlet and discharge pipes 19, 15 of the urine bag 2 are also formed during the knitting. Elastic threads are interknitted at either edge area of the web to form the elastic bands 9, 10, and further elastic threads (not shown) 21 are interknitted across the width of the web.

Between subsequent pockets in the first web 37 cutting lines 44 are formed extending transversely of the longitudinal direction 45 of the first web 37. The first web is cut up 46 at the cutting lines to form web sections 47. The two ends 31, 32 of the web sections 47 are subsequently joined by a seam 33 to form the tubular garment 1 having a size designed to fit snugly around the leg of a user. This means that the distance between subsequent cutting lines 44 varies depending on whether the garment is intended for children, for adults for positioning on a thigh, or for positioning on a leg below the knee.

It should be noted that not all details of the garment 1 are shown in FIG. 5 since that figure only serves to illustrate the principle of the method.

FIG. 6 illustrates a further embodiment, which differs from the one shown in FIG. 5 in that the first web 37 is interknitted with a second web 48 at one of its edge areas (at the band 9). Cutting lines 49 are formed in the second web 48 at a mutual distance that is larger than the distance between the cutting lines 44 in the first web 37. The second web is cut 50 at the cutting lines 49. The cuttings 46 and 50 of the first web 37 and the second web 48 are carried through to an intersection 51 of the two webs. During knitting, the opening 52 extending between subsequent cutting lines 44 is formed in said intersection 51 so that separate web sections 53 result from the cuttings 46, 50. The web sections 53 are substantially T-shaped. After the formation of the seam 33 and the seam 36 joining the two ends 34, 35 formed by cutting the second web 48, a garment 1 results, which may be conceived of as briefs having a long leg. After the cutting of the two webs 37, 48, the sheets 57 will be waste pieces that are not used.

FIG. 7 illustrates a further embodiment of the method. According to this embodiment, a second web 48 is placed on either side of the first web 37. In this manner all material is used since there is no waste corresponding to the sheets 57. In this further embodiment the web sections 53 are formed with alternating orientation. Owing to this arrangement the entire knitted webs are used since the length of the web sections 53 in the second web 48, measured between subsequent cutting lines 49, corresponds to the double length of the first web sections measured between subsequent cutting lines 44. As a consequence, there will be no waste in the embodiment shown in FIG. 7.

A common feature of all the garments and embodiments is that a number of openings 14, 17, 18 for the passage of the inlet and discharge pipes of the urine bag are formed in the pocket 11 and edge areas at the bottom and the top, and that at least across the height of the pocket 11 elastic threads 21, 27 are knitted in, arranged at a mutual distance and extending in the longitudinal direction of the web.

FIG. 8 illustrates a partial knitting diagram for the manufacture on a double Raschel knitting machine. The knitting diagram illustrates the manufacture of the embodiment of the garment 1 shown in FIG. 5.

FIG. 8 illustrates the knitting in an area 58 at the side of the web 12 intended to face the body of the use, whereas the area 59 illustrates the knitting on the other track for the formation of the side of the web 12 turning away from the body of the user. The area 60, 61 illustrates the area 40 in the first web 12 in which the pocket 11 is formed. The areas 62, 63 illustrate areas with ordinary interknitting of the yarns/threads from the two needle tracks. As the cutting line 44 is formed as a very traditional cutting line, the knitting of it is not illustrated.

It is seen that the bands 9, 10 are manufactured from elastic threads 64 extending transversely of several needle rows to form, in a manner known per se, an elastic band. The hole 14 is seen at the bottom 13 of the pocket, and a hole 17, 18 is seen in the upper edge area 16 of the pocket. The holes are formed in areas between elastic threads forming band-like areas, which, particularly in the bottom 13, provide a firm delimitation of the holes.

The briefs may be produced from different types of yarns, including in particular polyester and elastan. It will also be possible to knit in cotton in order to improve user comfort.

I claim:

1. A garment for fixing a urine bag on a leg of a user and comprising at least one tubular part to be positioned on the leg of the user and which is manufactured by knitting, the tubular part comprising at its ends elastic bands and a pocket having an upwardly oriented opening in a service position and a bottom oriented downwardly in a service position, the bottom having at least one opening for the passage of a discharge pipe of the urine bag, wherein the elastic bands are arranged to be able to carry a full urine bag, and wherein the pocket is produced as an integral part of the tubular part, which has a dual layer structure that is knitted together except in a central area for the pocket.

2. A garment according to claim 1, wherein the opening (13) in the pocket bottom (13) is located in a middle of the pocket.

3. A garment according to claim 1, wherein an edge area at the upwardly oriented pocket opening is provided with holes for the passage of the inlet pipe of the urine bag.

4. A garment according to claim 3, wherein at least one hole is located at a corner of the pocket that, when in use, will face an opposite user leg of the leg on which the garment is placed.

5. A garment according to claim 1, wherein at least over a height of the pocket elastic threads are knitted in at a mutual distance and extending in the circumferential direction of the tubular part.

6. A method for manufacturing a garment for fixing a urine bag on a leg of a user, wherein a first web is knitted on two needle tracks, wherein said first web is knitted of yarns from said two needle tracks except in a central area for a pocket having an upwardly oriented opening in a service position, wherein elastic bands are knitted at either edge area of the first web, wherein in a position between each subsequent pocket cutting lines are formed transversely of the knitted first web, wherein the first web is cut up in the cutting lines, and wherein ends of the web sections thus formed are assembled for the formation of a tubular garment having such size that it will fit snugly around the leg of a user.

7. A method according to claim 6, wherein at least one edge area the first web is knitted together with an additional web, and wherein cutting lines are found across said additional web at a larger mutual distance than the distance between the cutting lines of the first web that upon cutting and assembling of the ends formed the additional web will form a tubular shape intended to surround the waist area of the user.

8. A method according to claim 7, wherein on either side of the first web (48) an additional web (48) is knitted, and wherein the length of the web sections corresponds to the double of the length of the first web sections.

9. A method according to claim 6, wherein a number of openings are formed in the bottom and top edge area of the pocket for the passage of the inlet and discharge pipes of the urine bag.

10. A method according to claim 6, wherein at least over the height of the pocket elastic threads are knitted in, arranged at a mutual distance and extending in the longitudinal direction of the first web.

* * * * *